US012629493B2

(12) United States Patent
Lamuraglia

(10) Patent No.: US 12,629,493 B2
(45) Date of Patent: May 19, 2026

(54) PORTABLE ANESTHETIC DELIVERY DEVICE

(71) Applicant: Raul Lamuraglia, Buenos Aires (AR)

(72) Inventor: Raul Lamuraglia, Buenos Aires (AR)

( * ) Notice: Subject to any disclaimer, the term of this patent is extended or adjusted under 35 U.S.C. 154(b) by 667 days.

(21) Appl. No.: 18/151,109

(22) Filed: Jan. 6, 2023

(65) Prior Publication Data

US 2024/0226488 A1     Jul. 11, 2024

(51) Int. Cl.
*A61M 16/00* (2006.01)
*A61M 16/10* (2006.01)
*A61M 16/22* (2006.01)

(52) U.S. Cl.
CPC ...... *A61M 16/104* (2013.01); *A61M 16/0078* (2013.01); *A61M 16/22* (2013.01); *A61M 2016/0027* (2013.01); *A61M 2250/00* (2013.01)

(58) Field of Classification Search
CPC ............ A61M 16/104; A61M 16/0078; A61M 16/22; A61M 2016/0027; A61M 2250/00; A61M 16/00; A61M 16/04; A61M 16/0425
See application file for complete search history.

(56) References Cited

U.S. PATENT DOCUMENTS

| | | | | |
|---|---|---|---|---|
| 6,131,571 A | * | 10/2000 | Lampotang | ....... A61M 16/0069 |
| | | | | 128/204.23 |
| 6,619,289 B1 | * | 9/2003 | Mashak | ................ A61M 16/22 |
| | | | | 128/205.12 |
| 2009/0151724 A1 | * | 6/2009 | Wondka | ............ A61M 16/0463 |
| | | | | 128/204.23 |
| 2011/0297149 A1 | * | 12/2011 | Leonard | .............. A61M 16/209 |
| | | | | 128/203.14 |
| 2012/0037162 A1 | * | 2/2012 | Boussignac | ....... A61M 16/0833 |
| | | | | 128/207.14 |
| 2012/0103333 A1 | * | 5/2012 | Dingley | ............ A61M 16/0081 |
| | | | | 128/205.13 |
| 2014/0276178 A1 | * | 9/2014 | Simon | ................ A61M 16/0875 |
| | | | | 128/207.14 |
| 2015/0297857 A1 | * | 10/2015 | Blomberg | ............. A61M 16/01 |
| | | | | 128/203.14 |
| 2018/0093063 A1 | * | 4/2018 | Rajan | ................. A61M 16/0066 |
| 2021/0213220 A1 | * | 7/2021 | Brown | .................... B01D 15/40 |
| 2021/0322709 A1 | * | 10/2021 | Kopalli | ............. A61M 16/0051 |

* cited by examiner

*Primary Examiner* — Margaret M Luarca
*Assistant Examiner* — Sarah B Lederer
(74) *Attorney, Agent, or Firm* — Ware, Fressola, Barber & Maguire LLP

(57) ABSTRACT

A portable anesthetic delivery device includes a breathing circuit. The breathing circuit includes a container having a support member holding a carbon dioxide absorber configured to remove carbon dioxide generated during an anesthetic procedure. The container has an outlet port, an inlet port and a removable top portion. A connector assembly has a first unidirectional check valve that is detachably and airtightly connectable to the outlet port of the container via a first tube and a second unidirectional check valve that is detachably and airtightly connectable to the inlet port of the container via a second tube. A pressure sensor is attached to the top portion of the container. The pressure sensor is configured to measure pressure within the breathing circuit.

20 Claims, 7 Drawing Sheets

PORTABLE ANESTHETIC DELIVERY DEVICE

FIELD

The present disclosure relates generally to devices for controlling anesthesia, and more specifically to a portable anesthetic delivery device.

BACKGROUND

An anesthetic, or combination of anesthetics, may be delivered to a patient in order to produce the effects of sedation, analgesia, and neuro-muscular block, broadly referred to as anesthesia. Different anesthetics produce different effects and degrees of effects, and therefore, must be carefully delivered to the patient. Under established methods, a carrier gas (or a combination of carrier gases) is passed over a liquid inhalation anesthetic (or a combination of anesthetics) in a vaporizer, for delivery to the patient.

The inhalation anesthesia of animals not only plays a role in veterinary practice, but increasingly also in field use, for example on a farm. For example, the castration of piglets may no longer be carried out without anesthesia due to more stringent animal welfare regulations. Therefore, anesthetic delivery devices should be mobile, reliable and easy to use.

Conventional portable anesthesia devices are relatively cumbersome and expensive and the installation requires certain expertise. The high cost of the device has also prevented pet owners from buying their own facility.

Thus, improvements in anesthetic delivery devices that are reliable and easy to use and that can be used in a field with large animals are needed.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

A broad object of aspects of the disclosure is to provide a portable anesthesia device for animals, including but not limited to, large animals, which monitors the mixture of gases in a breathing circuit.

In an aspect, a portable anesthetic delivery device includes a breathing circuit. The breathing circuit includes a container having a support member holding a carbon dioxide absorber configured to remove carbon dioxide generated during an anesthetic procedure. The container has an outlet port, an inlet port and a removable top portion. A connector assembly has a first unidirectional check valve that is detachably and airtightly connectable to the outlet port of the container via a first tube and a second unidirectional check valve that is detachably and airtightly connectable to the inlet port of the container via a second tube. A pressure sensor is attached to the top portion of the container. The pressure sensor is configured to measure pressure within the breathing circuit.

In an aspect, a method of anesthetizing a large animal using a portable anesthetic delivery device as described herein. In a particular aspect, the method comprises providing an anesthesia agent into oxygen in the breathing circuit for delivery as a mixture to the large animal. Pressure is measured within the breathing circuit. A flow rate of the mixture is controlled based on the measured pressure as the mixture travels through the breathing circuit to the large animal so that the large animal receives a desired amount of anesthesia agent based on the controlled flow rate.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The disclosed aspects will hereinafter be described in conjunction with the appended drawings, provided to illustrate and not to limit the disclosed aspects, wherein like designations denote like elements, and in which.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known components may be shown in block diagram form in order to avoid obscuring such concepts.

Those skilled in the art will readily appreciate that the description given herein with respect to those figures is for explanatory purposes only and is not intended in any way to limit the scope of the disclosure. For example, while the preferred aspect of the disclosure is described with respect to a crossword cube game, those skilled in the art will appreciate that numerous other applications, games, and the like may be implemented in three dimensions on a computer video screen in accordance with the techniques of the disclosure. Accordingly, all questions regarding the scope of the disclosure should be resolved by referring to the claims.

The disclosed system is particularly adapted for use in procedures that are performed on animals that require the administration of anesthesia. Such procedures typically should be performed on a properly anesthetized animal to facilitate successful completion of the procedure and ensure humane treatment of the animal during the procedure. The apparatus of the present disclosure provides means for the controlled delivery of gaseous components for inhalation by animals, and means for the removal of gases exhaled by the animals. The gaseous components are delivered in a carrier medium, such as pressurized air, oxygen gas, or the like, which is infused with atomized or vaporized anesthetic components. The flow of anesthetic components may be controlled to achieve a concentration in the carrier medium that is sufficient to anesthetize a large animal. As used herein, the term "large animal" refers to an animal with average weight of at least one hundred pounds.

Advantageously, the disclosed device includes a flow sensor operative to determine a gas flow within the entire circuit. For example, the flow sensor may be a manometer. The disclosed anesthesia device is portable and may be used in a field. To maintain spontaneous breathing of a patient during the procedure a flow pressure should be maintained in a particular range.

Turning now to the figures, example aspects are depicted with reference to one or more components described herein, where components in dashed lines may be optional.

Figure 1:
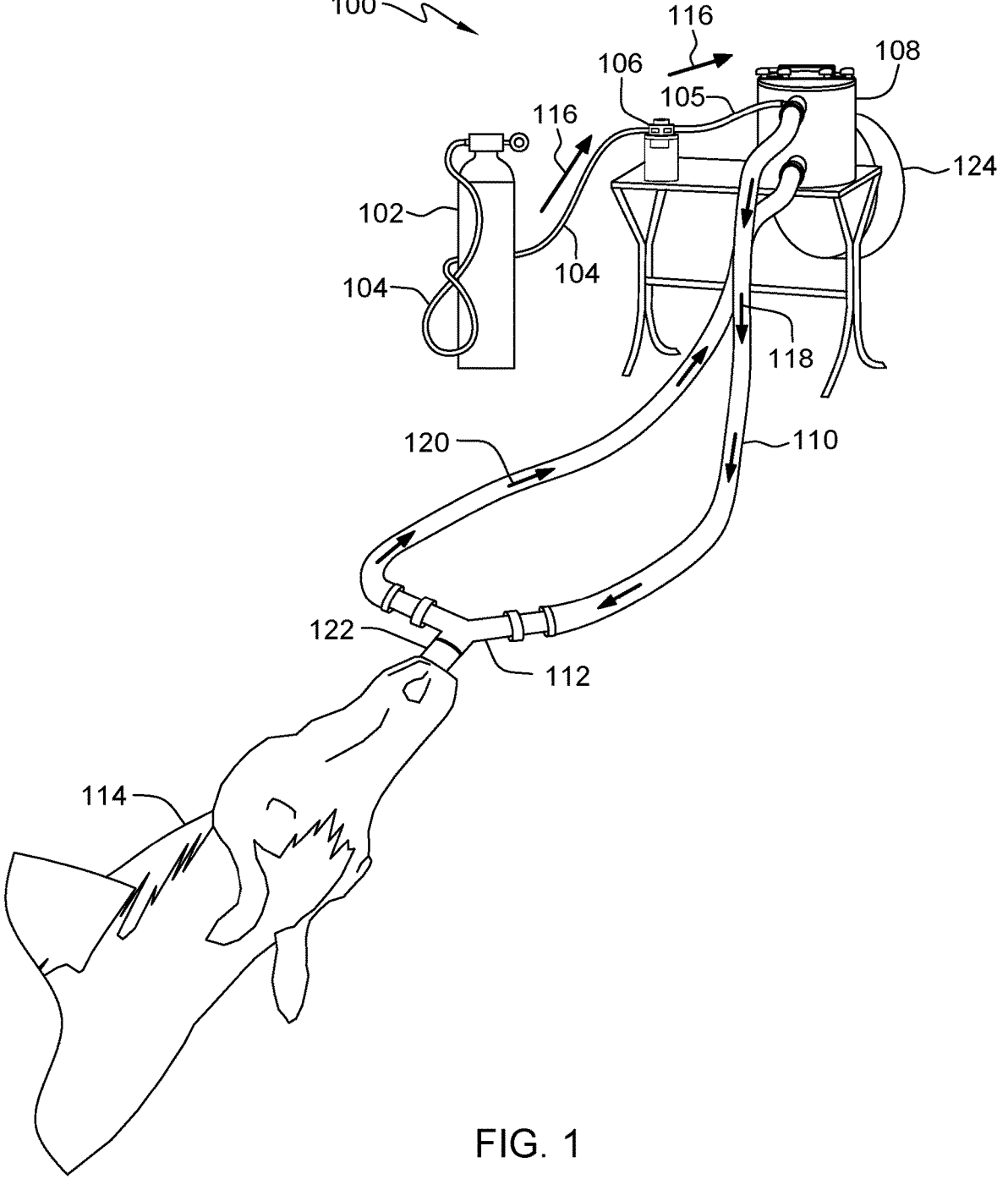
FIG. 1 shows an exemplary functional illustration of a portable anesthesia delivery system in accordance with one aspect of the present disclosure.

FIG. 1 shows an exemplary functional illustration of a portable anesthesia delivery system in accordance with one aspect of the present disclosure. For illustrative purposes, working-pressure oxygen flow arrows 116, combined anesthesia gas and oxygen flow arrows 118, and exhalation gases flow arrows 120 are provided to help illustrate the flow of gases through system 100 when all control valves are open and gases flow freely.

As shown in FIG. 1, the delivery system 100 includes a pressurized source 102 of oxygen. In an aspect, the source of oxygen 102 may be a pressurized oxygen tank, although other sources of high concentration oxygen might be used, including, but not limited to, liquid oxygen or oxygen from a concentrator, all of which are comprehended by this disclosure as well. Oxygen source 102 delivers oxygen at a pressure determined by the outlet pressure of an oxygen source that conduit 104 is coupled to. For example, oxygen pressure may be supplied according to the outlet pressure of the tank 102 (up to about 3 to about 10 liters/minute set with the flowmeter). Within system 100, oxygen may perform one or more of the following tasks: act as a carrier for an anesthesia gas, life sustainment for a patient 114 associated with the portable anesthesia delivery system 100, and a meter for flowmeter measurement.

In an aspect, oxygen output from oxygen source 102 may travel via conduit 104 to vaporizer 106. The present disclosure includes an anesthesia gas source or similar device that provides a controllable level of an anesthesia gas or agent. As the term is used herein, an anesthesia gas refers to any gas or agent that is used to induce any level of anesthetic state, unconsciousness, lack of awareness, or local or general insensibility to pain for the patient 114 interacting with the portable anesthetic delivery device 100. Vaporizer 106 may be an anesthesia gas source that adds an anesthesia gas to low-pressure oxygen and may include an inlet that receives low-pressure oxygen from the oxygen source 102. The output of vaporizer 104 typically comprises a controlled and variable gas mixture of life sustaining gases and anesthetizing gases. In a specific aspect, vaporizer 106 may add isoflurane to low pressure oxygen received from the oxygen source 102 by passing the oxygen across a vaporizer that evaporates isoflurane. In this case, the low-pressure oxygen acts as a carrier for the anesthesia gas, which is added to the oxygen according to the physical characteristics of the anesthesia liquid and its temperature. The output from the vaporizer 106 may travel via conduit 105 to the container 108. Vaporizer 106 may employ one or more variable bypass, flow over, temperature compensated, and/or agent-specific vaporization techniques. Although the example described above with respect to vaporizer 106 added only a single anesthesia gas, isoflurane, it is understood that an anesthesia gas source of the present invention may add multiple anesthesia gases, as one of skill in the art will appreciate. A VIP 3000 veterinary anesthetic TEC 3-style vaporizer may be suitable for use as vaporizer 106.

In an aspect, the portable anesthesia delivery system 100 may further include a breathing circuit which may be positioned between the outlet of the vaporizer 106 and the patient attachment piece 122 which delivers the gas to the patient 114. In an aspect, the patient attachment piece 122 may comprise an endotracheal tube or a tracheostomy tube. Intubation of a patient is a procedure which is useful, yet potentially harmful if not controlled.

In an aspect, the breathing circuit may include connector assembly, referred to hereinafter as a Y-junction 112 which may separate the breathing circuit into an inhalation branch and an exhalation branch of the breathing circuit. The exhalation branch 112 carries exhalation gases from the Y-junction 112 toward a container 108. Such exhalation gases may include, but are not limited to, air, nitrogen, $O_2$, $CO_2$, other trace elements present in the inhaled air, as well as anesthetic agents.

Object of the present disclosure is to provide a generic portable device for supplying a patient, especially a spontaneously breathing patient, with a gas that allows optimization of gas consumption in a variety of spontaneously breathing patients. Anesthetic parameters, which may influence the patient's compliance with the procedure, such as the inhalative and the exhalative respiratory resistance, should not be significantly influenced. The disclosed breathing circuit is particularly suited for veterinary use, but may be adapted for human use as well.

As shown in FIG. 1, a container 108, such as, but not limited to a carbon dioxide absorber cannister, may be connected to the exhalation branch to remove the $CO_2$ from the gas stream. After the $CO_2$ content of the exhaled gas is removed, using a chemical reaction, by the container 108, the remaining gases in the exhalation branch are united or mixed with the gases in the inhalation branch to deliver to the patient 114 a combination of the scrubbed anesthetic agent from the exhalation branch with fresh anesthetic gas from the vaporizer 106.

In an aspect, the container 108 may contain a carbon dioxide ($CO_2$) absorber, such as a soda lime. Soda lime is widely used in the anesthesia field to absorb $CO_2$ from the breathing systems developed in the field. There are different compositions of soda lime in use today but the main component in all of them are calcium hydroxide $Ca(OH)_2$, also mentioned as slaked lime. Most of the brands also contain NaOH.

Advantageously, the body portion of the container 108 may be formed of a corrosion resistant metal also selected for strength to protect the contents of the carbon dioxide absorber canister 108, such as stainless steel as one non-limiting example.

In an aspect, the container 108 may be connected to the Y piece 112 via the inhalation tube 110a and exhalation tube 110b. The inhalation tube 110a and exhalation tubes 110b may be corrugated to have a single length, while permitting the length of the tube 110 to be expanded, or contracted. In an aspect, the length of the corrugated inhalation tube 110a and exhalation tube 110b in the fully expanded form may range from about 1.8 meters to about 2.8 meters.

The variability of the length of the corrugated inhalation 110a and exhalation 110b tubes permits the length of the tubes to be stretched (lengthened) and compressed (shortened) for short periods of time. This variation in length often occurs when the relative position of the patient 114 and the container 108 is changed, and usually involves the need to stretch the tube during this change in relative position.

Figure 3:
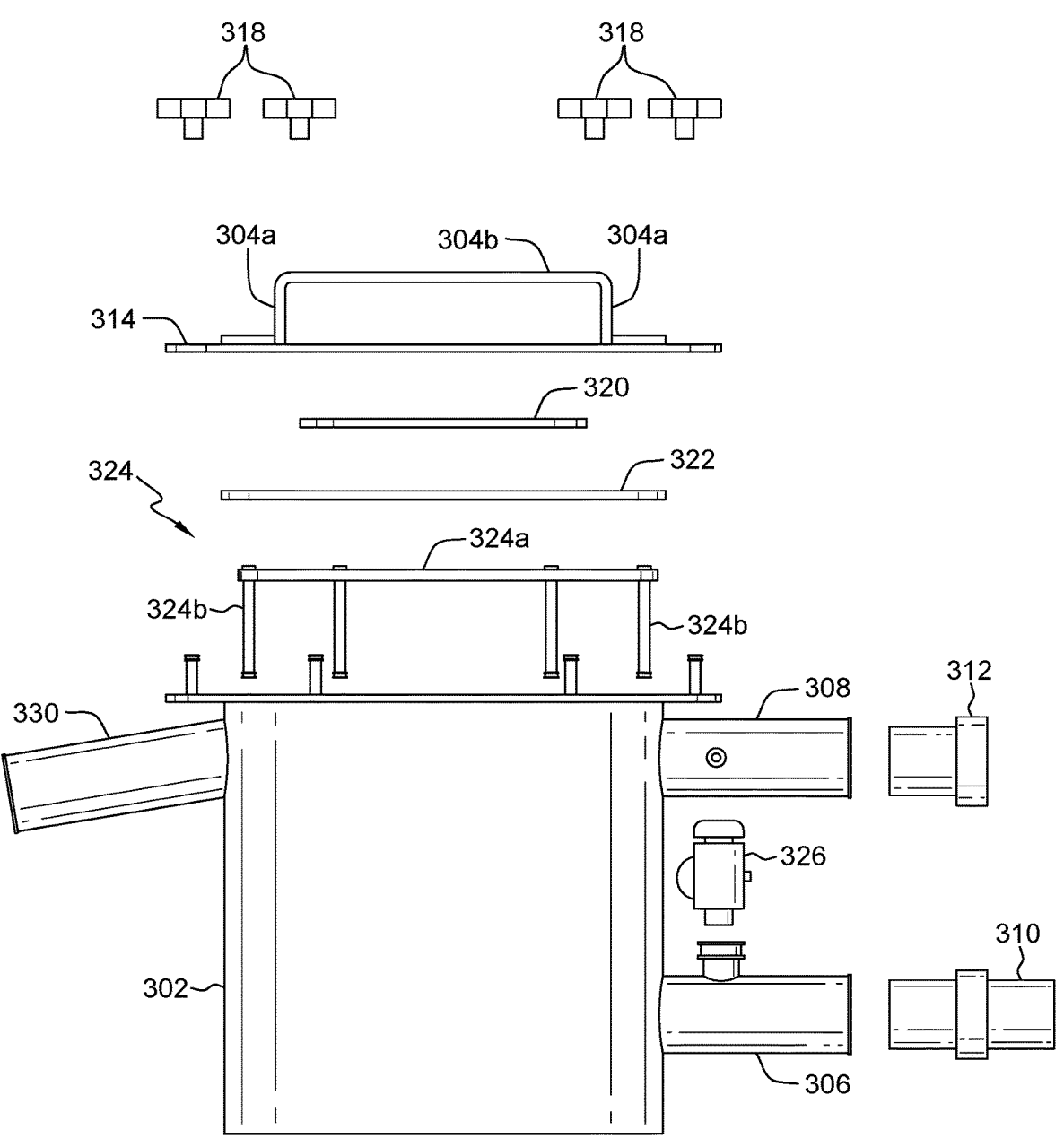
FIG. 3 is an exploded perspective view of a carbon dioxide absorption canister, in accordance with one aspect of the present disclosure.

A breathing bag 124 may be connected to the carbon dioxide absorber canister 108 via a port 330 shown in FIG. 3. The breathing bag 124 may provide an expandable volume for accommodating the exhaled and fresh gas entering the system, customarily used as a part of the lung ventilating system. The breathing bag 124 may be flow connected to the canister 108 via port 330. The breathing bag 124 may inflate as the patient exhales and deflate as the patient inhales, and may allow for "bagging" of the patient if necessary. Manipulation of the bag by the application of hand pressure affords a valuable indication as to whether proper lung ventilation is taking place, according to the feel provided by the bag 124. That is to say, the bag pressure along with other indicators reveals to an experienced anesthetist whether lung ventilation is proceeding in a satisfactory manner.

In summary, a method of anesthetizing a large animal using a portable anesthetic delivery system 100 as described herein is provided. In a particular aspect, the method includes connecting a breathing circuit to the patient attachment piece 122 which delivers the gas to the patient 114 (e.g., large animal). An anesthesia gas source (e.g., vaporizer 106) may be fluidly coupled to a container component (e.g. container 108) of the breathing circuit. The container component 108 may be configured to remove carbon dioxide generated during an anesthetic procedure. An anesthesia agent may be provided into oxygen in the breathing circuit for delivery as a mixture to the large animal 114. Pressure may be measured within the breathing circuit. A flow rate of the mixture may be controlled as the mixture travels through the breathing circuit to the large animal 114 so that the large animal 114 receives a desired amount of anesthesia agent based on the controlled flow rate.

Figure 2:
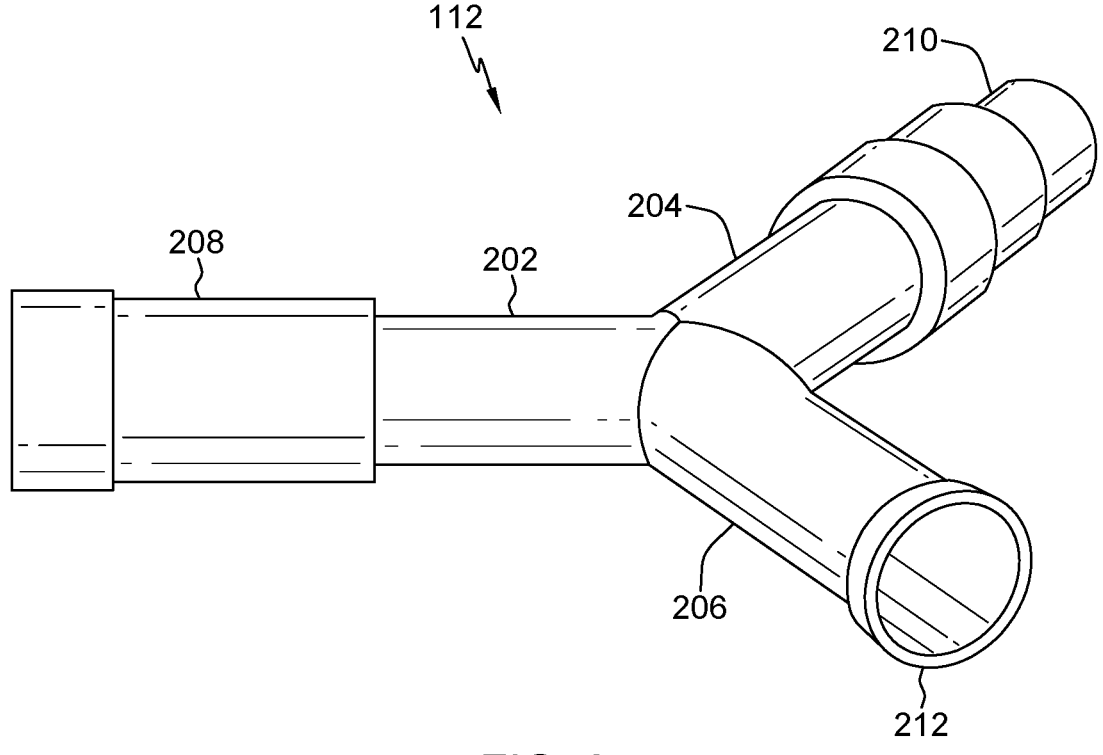
FIG. 2 is a perspective view of a connector assembly of the portable anesthesia delivery system; according to some present aspects.

FIG. 2 is a perspective view of a Y-piece of the portable anesthesia delivery system 100, according to some present aspects.

As used in connection with the present disclosure, the expression "Y-piece" also includes shapes other than that of conventional "Y." Of significance is only the fact that the patient attachment piece 122 can be connected to the inhalation 110a and exhalation 110b tube, respectively. The expression "Y-piece" thus also includes, for example, T-connectors and connectors for coaxially connecting arranged inhalation 110a and exhalation 110b tubes.

The Y-piece 112 shown in FIG. 2 may comprise three interconnected member parts 202-206. The first member 202 may be provided with a first nipple 208 which is intended to be connected to the patient attachment piece 122. The second member 204 may be provided with a second nipple

210, which is intended to be connected to the exhalation tube 110b. The third member 206 may be provided with a third nipple 212, which is intended to be connected to the inhalation tube 110a. In an aspect, each of the nipples 208-212 is preferably provided with an inner or outer screw thread, or other such fixing means. In an aspect, the first nipple 208 may be a female nipple and the second nipple 210 may be a male nipple.

In an aspect, the second nipple 210 and the third nipple-212 may be provided with unidirectional valve means or a valve which prevents gas flow from the opposite side of the circuit to pass therethrough. For example, the commingled gases are directed through the inhalation tube 110a, the third nipple 212, the first nipple 208, the attachment piece 212 to the patient's 114 lungs. Upon exhaling by the patient 114, the gas flow is reversed. The reverse gas flow then flows from the patient's lungs through attachment piece 212, the first nipple 208, the second nipple 210 to exhalation tube 110b. The unidirectional valve provided by the third nipple 212 prevents this reverse flow from passing through the inhalation tube 110a. The reverse gas flow is thereby forced to travel through the Y piece 212 to the carbon dioxide absorber canister 108. Similarly, the unidirectional valve provided by the second nipple 210 prevents inhalation gasses from passing through the exhalation tube 110b.

Advantageously, the first 202, second 204 and third 206 members may be formed of a corrosion resistant metal also selected for strength, such as stainless steel as one non-limiting example. The first 208, second 210, and third 212 nipples may be formed of a polymer composite such as resin as one non-limiting example. Preferably, the valve members may be made of a hard plastic, including, for example and without limitation, ABS, polypropylene, polyethylene, or PVC.

FIG. 3 is an exploded perspective view of the carbon dioxide absorption canister 108, in accordance with one aspect of the present disclosure. The carbon dioxide absorber canister 108 is attached to and is in fluid communication with the closed circuit supply of gases to remove carbon dioxide from the patient gas. The absorber canister 108 may contain the carbon dioxide absorber containing soda lime granules that removes carbon dioxide from the gas before it is breathed on the next cycle. In an aspect, the carbon dioxide absorber may be replaced during the procedure without interrupting the anesthesia (for example, every 8 hours).

As shown in FIG. 3, the absorber canister 108 may have essentially cylindrical in shape body portion 302. The absorber canister 108 may include a handle 304 arranged to be manually grasped by the caregiver. In an aspect, one side of the body portion 302 of the canister 12 may include an inlet port 306 and outlet port 308 that are configured to be compatible and fluidly coupled to inhalation tube 110a and exhalation tube 110b, respectively, which are shown in FIG. 1. Advantageously, the body portion 302, the handle 304, as well the inlet port 306 and the outlet port 308 of the container 108 may be formed of a corrosion resistant metal also selected for strength to protect the contents of the canister 108, such as stainless steel as one non-limiting example.

In an aspect, the inlet port 306 may be provided with a first nipple 310 which is intended to be connected to the exhalation tube 110b. The outlet port 308 may be provided with a second nipple 312, which is intended to be connected to the inhalation tube 110a. In an aspect, each of the nipples 310-312 is preferably provided with an inner or outer screw thread, or other such fixing means. In an aspect, the first nipple 310 may be a male nipple and the second nipple 312 may be a female nipple.

In an aspect, a generally inverted U-shaped handle 304 may extend upwardly from the top portion 314 of the canister 108. The handle 304 may include arms 304a extending upwardly from the top portion 314 and a gripping portion 304b that may extend between the arms 304a. An opening 702 (shown in FIG. 7) may be formed in the top portion 314, and may be positioned such that the contents of the canister 108 will at least be visible through the opening 702. The handle arms 304a may be sized such that there is a space between the handle gripping portion 304b and the top portion 314, to enable an operator to easily grasp the handle gripping portion 304b to lift and carry the canister 108.

In an aspect, the top portion 314 may further include slides or levers 318 which when twisted, release the locking mechanism to allow the top portion 314 to be lifted away from the body portion 302 of the canister 108.

In an aspect, one or more layers of transparent stretched acrylic sheets may be formed inside the opening 702. In an aspect, a first acrylic sheet 320 may have controlled solar energy transmission properties. The transparent stretched acrylic sheet 320 may be formed from a thermoplastic acrylic polymer or any other IR absorbing material having the ability to preferentially absorb solar energy between the wavelengths of about 700 nm to about 1100 nm. The IR absorbing material reduces the ratio of IR light to visible light transmitted through the stretched acrylic sheet 320. Because less IR light is transmitted through the stretched acrylic sheet 320 for a given amount of visible light, less heat is transmitted through the stretched acrylic sheet 320. This phenomenon is desirable to control the environments of the content of the canister 108. The IR absorbing material may include a perylene based dye and/or a hexaboride based nanoparticle IR absorber.

In an aspect, an optional second acrylic layer 322 can be attached to the light absorbing acrylic layer 320. The second acrylic layer 322 can be the same or different than the first acrylic layer 320, but the second acrylic layer 322 can be a perforated acrylic layer.

In an aspect, the canister 108 may further include an insertable support member 324 that may be inserted into the canister 108, when the top portion 314 is removed. In an aspect, the support member 324 may include a horizontal base 324a and at least one pair of vertical legs 324b extending downwardly from the lower portion of the horizontal base 324a. In an aspect, the support member may be positioned to hold a carbon dioxide absorber material. In an aspect, the support member 324 may be inserted so that lower surface of the legs 324b touches an inner bottom (floor) portion 502 of the canister 108 (shown in FIG. 5). Advantageously, the support member 324 may be formed of a corrosion resistant metal also selected for strength to protect the contents of the canister 108, such as stainless steel as one non-limiting example.

In an aspect, a pressure relief valve 326 may be removably secured and flow connected to the inlet port 306. Therefore, the pressure relief (or pop-off) valve 326 may communicate with the breathing system and may evacuate excess gas from the breathing circuit to compensate for the fresh gas entering the circuit when pressure in the circuit exceeds a predetermined level. Since the portable anesthetic device 100 may be used primarily in outdoor environment, the vented gas may be released to the atmosphere.

In an aspect, a Positive End Expiratory Pressure (PEEP) valve (not shown in FIG. 3) may be connected to the pressure relief valve 326 to provide resistance based on PEEP by providing a pneumatic signal and thereby controlling the PEEP at the end of the exhalation of the patient's breath.

In an aspect, a flow sensor 802 (shown in FIG. 8) operative to determine a gas flow within the entire circuit may also be flow connected to the top portion 314 via port.

Figure 4:
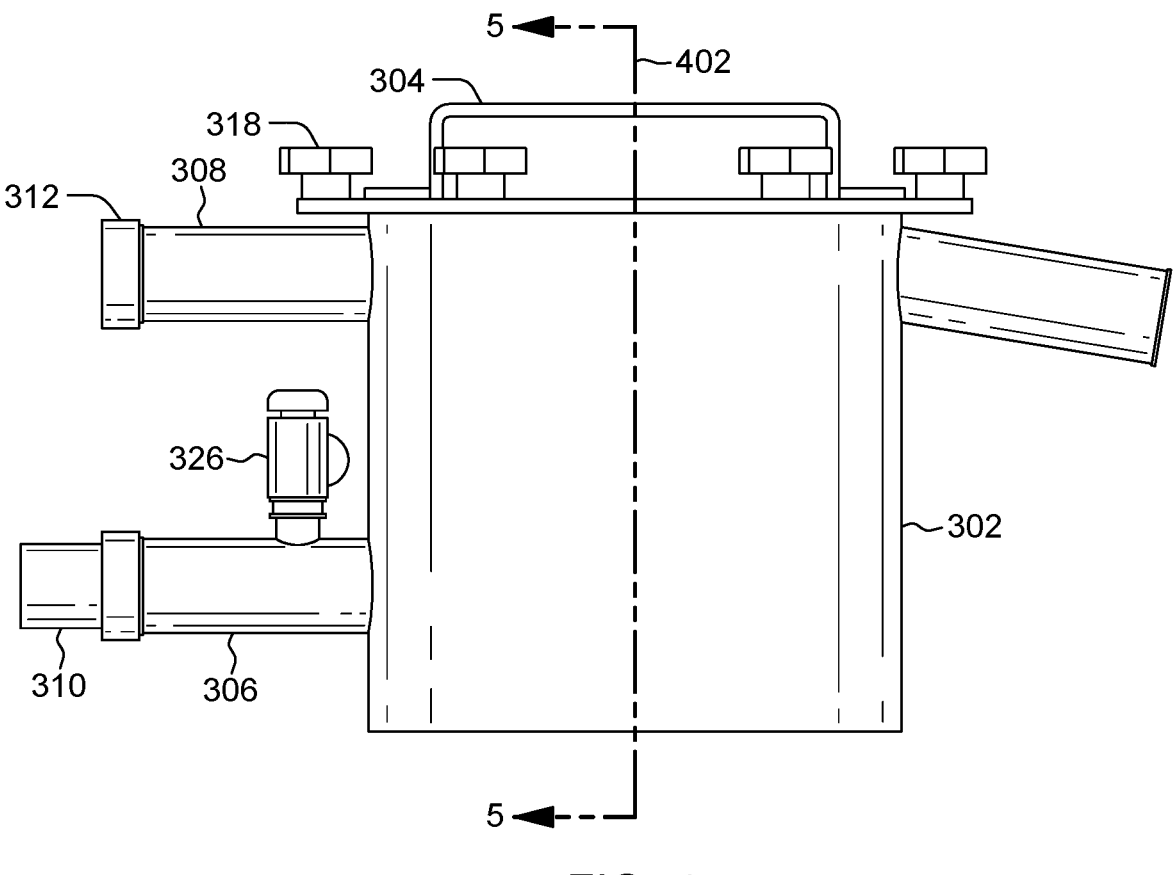
FIG. 4 is a side view of the carbon dioxide absorption canister, in accordance with one aspect of the present invention.

FIG. 4 is a side view of the carbon dioxide absorption canister, in accordance with one aspect of the present invention.

Figure 5:
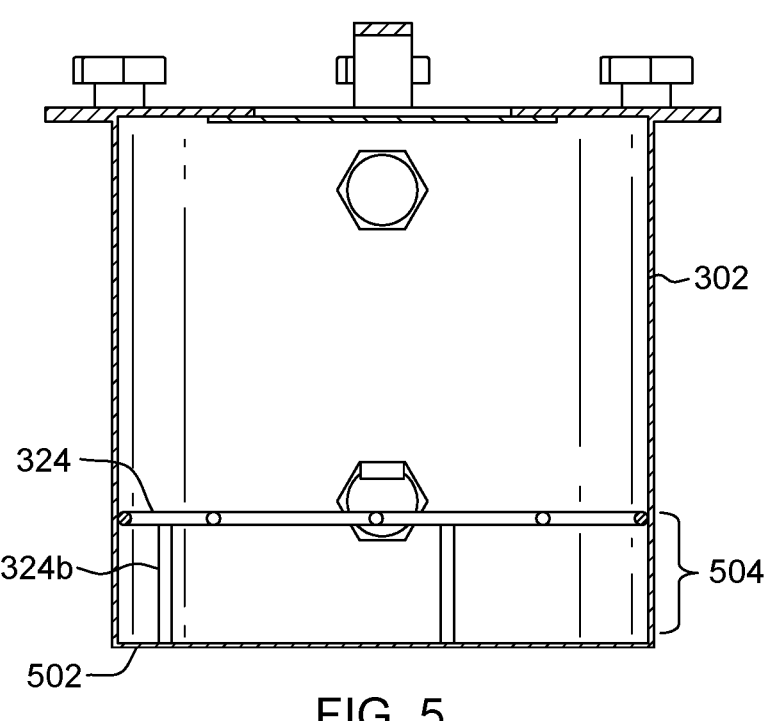
FIG. 5 is a cross-sectional view of the carbon dioxide absorption canister taken on the line A of FIG. 4, in accordance with one aspect of the present disclosure.

FIG. 5 is a cross-sectional view of the carbon dioxide absorption canister taken on the line 402 of FIG. 4, in accordance with one aspect of the present disclosure. FIG. 5 illustrates the support member 324 may be positioned to hold a carbon dioxide absorber material. In an aspect, the support member 324 may be inserted so that lower surface of the legs 324b touches an inner bottom (floor) portion 502 of the canister 108. In an aspect, the lower portion of the canister 504 essentially below the base 324a of the support member may comprise an air exchange chamber. In an aspect, the air exchange chamber optimizes movement of the aforementioned gasses within the canister 108, while dissipating heat and humidity.

Figure 6:
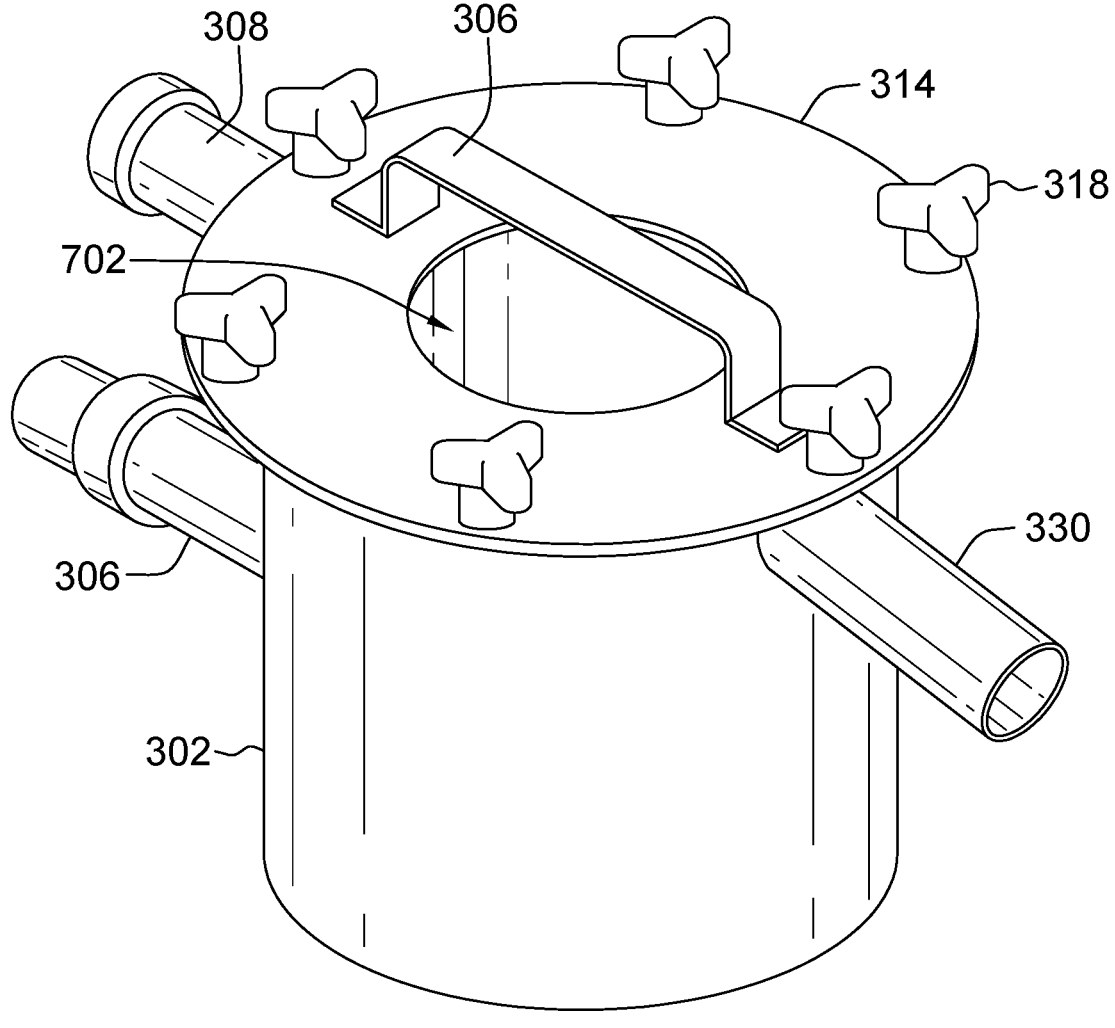
FIG. 6 is an isometric view of the carbon dioxide absorption canister, in accordance with one aspect of the present disclosure.

FIG. 6 is an isometric view of the carbon dioxide absorption canister, in accordance with one aspect of the present disclosure.

Figure 7:
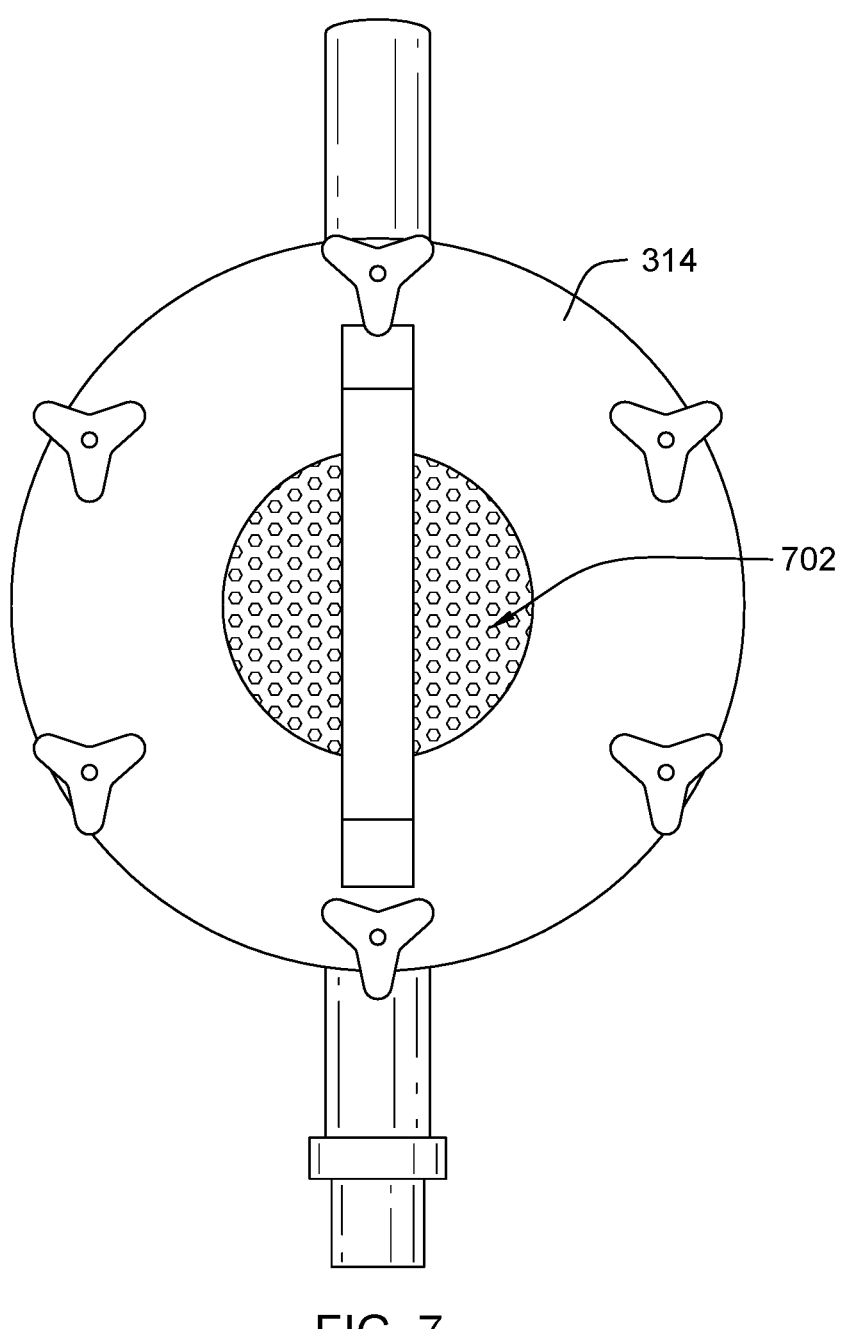
FIG. 7 is a top view of the carbon dioxide absorption canister, in accordance with one aspect of the present disclosure.

FIG. 7 is a top view of the carbon dioxide absorption canister, in accordance with one aspect of the present disclosure. An opening 702 may be formed in the top portion 314, and may be positioned such that the contents of the canister 108 will at least be visible through the opening 702. In an aspect, the opening 702 may have generally circular shape. The opening 702 may extend essentially from a center of the top portion 314. The circular shape of the opening 702 shown in the drawings is illustrative only; the opening 702 can be any shape. Through the opening 702, the operator can thus observe when the color of the $CO_2$ absorber changes during an operation, which in turn enables an operator to replace the $CO_2$ absorber. As noted above, the $CO_2$ absorber may be changed every 8 hours, for example.

Figure 8:
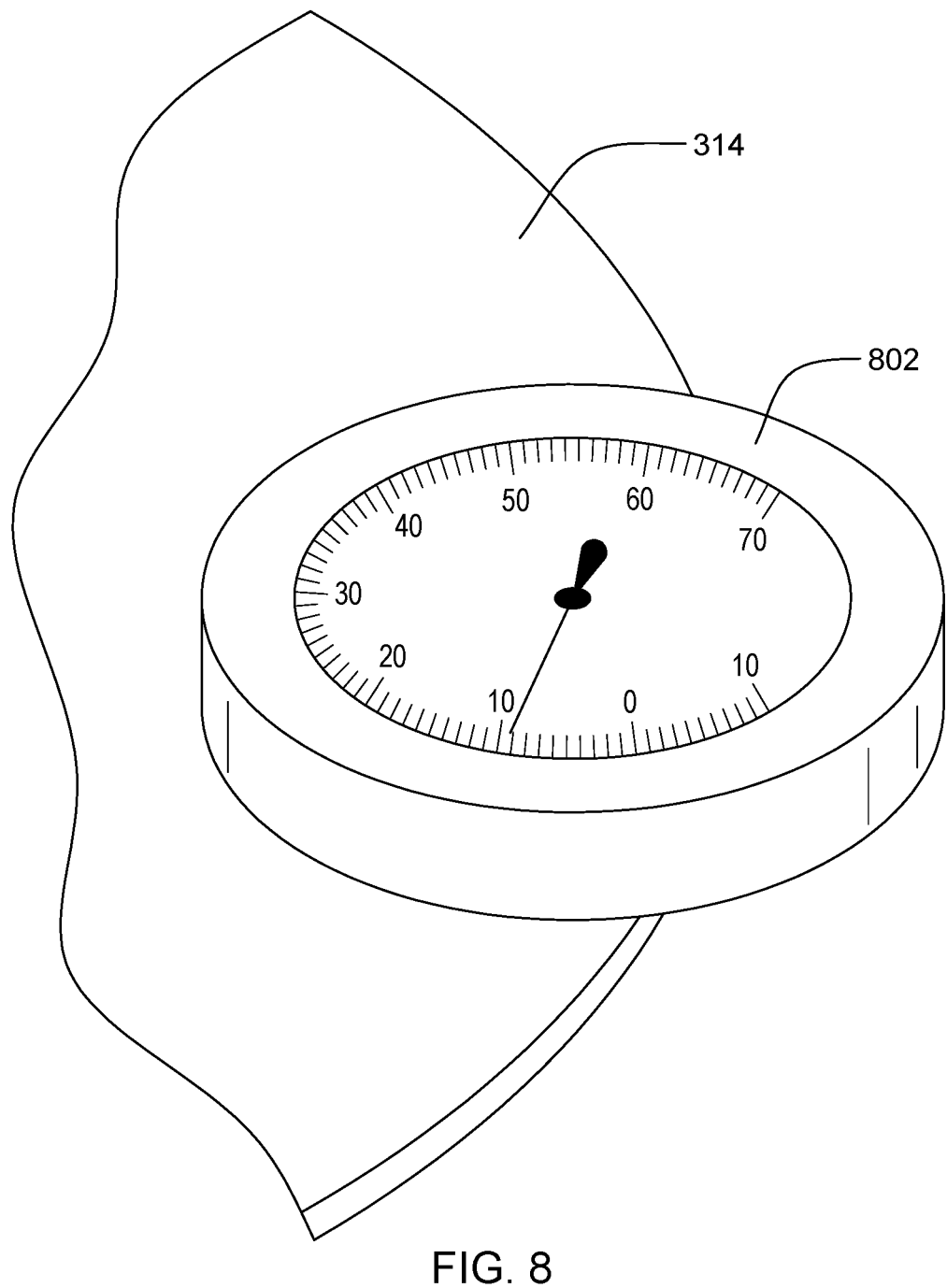
FIG. 8 is a partial view of the top portion of the carbon dioxide absorption canister of FIG. 3 having a flow sensor operative to determine a gas flow within the entire circuit, in accordance with one aspect of the present disclosure.

FIG. 8 is a partial view of the top portion of the carbon dioxide absorption canister having of FIG. 3 having a flow sensor operative to determine a gas flow within the entire circuit attached thereto, in accordance with one aspect of the present disclosure. In an aspect, the flow sensor may be a manometer 802 that may also be flow connected to the top portion 314 via port.

The manometer 802 may provide a visual reading of the pressure in the breathing circuit and may assist in setting the desired pressure threshold setting of the pressure relief valve 326. The manometer may allow for pressure readings between 0 and 80 centimeters of water. However, pressure readings of up to 30 centimeters of water are more than adequate, particularly since pressures above 20 centimeters of water may detrimentally affect the patient's lungs. Furthermore, the manometer 802 may be finely-calibrated to provide a much more precise pressure reading than conventional manometers.

In summary, the disclosed portable anesthetic delivery device 100 employs highly advantageous materials, such as stainless steel for the canister 108 element and the Y piece element 112 of the disclosure, due to its very high resistance to corrosion and high strength. When stainless steel is used to form essential elements of the anesthetic delivery device 100, it is found that the strength of this material allows the portable device to be essentially unbreakable during transportation and use in a field. In addition, the disclosed portable anesthetic delivery device 100 is easy to transport and easy to assemble.

It is to be understood that the phraseology or terminology used herein is for the purpose of description and not of restriction, such that the terminology or phraseology of the present specification is to be interpreted by the skilled in the art in light of the teachings and guidance presented herein, in combination with the knowledge of those skilled in the relevant art(s). Moreover, it is not intended for any term in the specification or claims to be ascribed an uncommon or special meaning unless explicitly set forth as such.

The invention claimed is:

1. A portable anesthetic delivery device, comprising:
a breathing circuit having:
a container having a support member holding a carbon dioxide absorber configured to remove carbon dioxide generated during an anesthetic procedure, the container having an outlet port, an inlet port and a removable top portion, wherein the removable top portion of the container has an opening formed therein, and wherein a first layer of a transparent infrared absorbing material is positioned inside the opening;
a connector assembly having a first unidirectional check valve that is detachably and airtightly connectable to the outlet port of the container via a first tube and a second unidirectional check valve that is detachably and airtightly connectable to the inlet port of the container via a second tube, wherein the connector assembly comprises a three-way Y-junction having a first member, a second member and a third member, wherein the first unidirectional check valve is fluidly coupled to the third member and positioned between the three-way Y-junction and the first tube without a change in direction along a length of the third member until connection with the first tube, and wherein the second unidirectional check valve is fluidly coupled to the second member and positioned between the three-way junction and the second tube without a change in a direction along a length of the second member until connection with the second tube; and
a pressure sensor attached to the top portion of the container, the pressure sensor configured to measure pressure within the breathing circuit.

2. The portable anesthetic delivery device of claim 1, wherein the first tube and the second tube comprise corrugated tubes.

3. The portable anesthetic delivery device of claim 1, wherein the portable anesthetic delivery device is configured to be connected to a spontaneously breathing non-human animal patient under sedation during the anesthetic procedure.

4. The portable anesthetic delivery device of claim 1, wherein the container and the connector assembly are each formed from a unibody stainless steel layer.

5. The portable anesthetic delivery device of claim 1, wherein each of the first unidirectional check valve and second unidirectional check valve are each formed from a thermoplastic resin.

6. The portable anesthetic delivery device of claim 1, wherein the carbon dioxide absorber is in a granular form.

7. The portable anesthetic delivery device of claim 1, wherein the first tube comprises an inhalation tube that delivers the inhalant gas from the outlet port of the container to the patient during inspiration and wherein the second tube comprises an exhalation tube that delivers expired air from the patient to the inlet port of the container, and wherein the first tube and the second tube are arranged side-by-side.

8. The portable anesthetic delivery device of claim 1, further comprising a third tube fluidly coupled to the first member of the three-way Y-junction of the connector assembly, wherein the third tube comprises an endotracheal tube.

9. The portable anesthetic delivery device of claim 1, further comprising an auxiliary gas port to facilitate connection of a pressurized oxygen source to the container and wherein the container is configured to combine oxygen with the inhalant gas.

10. A method of anesthetizing a large animal, comprising the steps of:
providing an anesthesia agent into oxygen in a breathing circuit for delivery as a mixture to the large animal during an anesthetic procedure;
measuring pressure within the breathing circuit; and
controlling a flow rate of the mixture based on the measured pressure as the mixture travels through the breathing circuit to the large animal so that the large animal receives a desired amount of anesthesia agent based on the controlled flow rate;
wherein the breathing circuit comprises
a container having a support member holding a carbon dioxide absorber configured to remove carbon dioxide generated during an anesthetic procedure, the container having an outlet port, an inlet port and a removable top portion and is connected to an anesthesia gas source, wherein the removable top portion of the container has an opening formed therein, and wherein a first layer of a transparent infrared absorbing material is positioned inside the opening;
a connector assembly having a first unidirectional check valve that is detachably and airtightly connectable to the outlet port of the container via a first tube and a second unidirectional check valve that is detachably and airtightly connectable to the inlet port of the container via a second tube, wherein the connector assembly comprises a three-way Y-junction having a first member, a second member and a third member, wherein the first unidirectional check valve is fluidly coupled to the third member and positioned between the three-way Y-junction and the first tube without a change in direction along a length of the third member until connection with the first tube, and wherein the second unidirectional check valve is fluidly coupled to the second member and positioned between the three-way junction and the second tube without a change in a direction along a length of the second member until connection with the second tube; and
a pressure sensor attached to the top portion of the container, the pressure sensor configured to measure pressure within the breathing circuit.

11. The method of claim 10, further comprising:
connecting the breathing circuit to an attachment device to which the large animal is connected.

12. The method of claim 11, wherein the attachment device comprises an endotracheal tube.

13. The method of claim 10, wherein controlling the flow rate comprises ventilating the large animal using a breathing bag connected to the container component of the breathing circuit, wherein the breathing bag is configured to inflate as the large animal exhales and configured to deflate as the large animal inhales.

14. The method of claim 10, further comprising connecting an oxygen source to the anesthesia gas source.

15. The portable anesthetic delivery device of claim 1, wherein the transparent infrared absorbing material is configured to absorb solar energy between wavelengths of about 700 nm and about 1100 nm.

16. The portable anesthetic delivery device of claim 1, further comprising a second layer of a transparent infrared absorbing material is positioned inside the opening.

17. The portable anesthetic delivery device of claim 1, wherein the transparent infrared absorbing material is a thermoplastic acrylic polymer.

18. The portable anesthetic delivery device of claim 16, wherein the second layer is a perforated acrylic layer.

19. A portable anesthetic delivery device, comprising:

a breathing circuit having:

a container having a support member holding a carbon dioxide absorber configured to remove carbon dioxide generated during an anesthetic procedure, the container having an outlet port, an inlet port and a removable top portion, wherein the removable top portion of the container has an opening formed therein, and wherein a first layer of a transparent infrared absorbing material is positioned inside the opening;

a connector assembly having a first unidirectional check valve that is detachably and airtightly connectable to the outlet port of the container via a first tube and a second unidirectional check valve that is detachably and airtightly connectable to the inlet port of the container via a second tube; and a pressure sensor attached to the top portion of the container, the pressure sensor configured to measure pressure within the breathing circuit.

20. The portable anesthetic delivery device of claim 19, wherein the transparent infrared absorbing material is configured to absorb solar energy between wavelengths of about 700 nm and about 1100 nm.

*    *    *    *    *